(12) United States Patent
Onyemauwa et al.

(10) Patent No.: US 11,045,773 B2
(45) Date of Patent: Jun. 29, 2021

(54) SALT TOLERANT POROUS MEDIUM

(71) Applicant: Pall Corporation, Port Washington, NY (US)

(72) Inventors: Frank Onyemauwa, Pace, FL (US); Hassan Ait-Haddou, Gulf Breeze, FL (US)

(73) Assignee: Pall Corporation, Port Washington, NY (US)

( * ) Notice: Subject to any disclaimer, the term of this patent is extended or adjusted under 35 U.S.C. 154(b) by 92 days.

(21) Appl. No.: 16/119,590

(22) Filed: Aug. 31, 2018

(65) Prior Publication Data
US 2020/0070104 A1 Mar. 5, 2020

(51) Int. Cl.
*B01D 71/56* (2006.01)
*B01D 69/10* (2006.01)
*B01D 71/26* (2006.01)
*C07K 1/34* (2006.01)

(52) U.S. Cl.
CPC ............. *B01D 71/56* (2013.01); *B01D 69/10* (2013.01); *B01D 71/26* (2013.01); *C07K 1/34* (2013.01); *B01D 2323/30* (2013.01); *B01D 2323/40* (2013.01); *B01D 2325/02* (2013.01)

(58) Field of Classification Search
CPC .... B01D 71/56; B01D 69/10; B01D 2323/30; C07K 1/34
See application file for complete search history.

(56) References Cited

U.S. PATENT DOCUMENTS

| | | |
|---|---|---|
| 5,453,186 A | 9/1995 | Müller et al. |
| 6,780,327 B1 | 8/2004 | Wu et al. |
| 6,783,937 B1 | 8/2004 | Hou et al. |
| 7,582,684 B2 | 9/2009 | Rasmussen et al. |
| 7,662,930 B2 | 2/2010 | Zhou |
| 8,114,611 B2 | 2/2012 | Bian et al. |
| 8,367,809 B2 | 2/2013 | Childs et al. |
| 8,658,702 B2 | 2/2014 | Diallo et al. |
| 8,673,988 B2 | 3/2014 | Graalfs et al. |

(Continued)

FOREIGN PATENT DOCUMENTS

| | | |
|---|---|---|
| AU | 2011203555 A1 | 8/2011 |
| CN | 10646027 A | 2/2017 |

(Continued)

OTHER PUBLICATIONS

European Patent Office, Examination Report issued in European Application No. 19193282.1 (dated Jan. 21, 2020).

(Continued)

*Primary Examiner* — Ellen M McAvoy
(74) *Attorney, Agent, or Firm* — Leydig, Voit & Mayer, Ltd.

(57) ABSTRACT

Disclosed is a porous medium, e.g., a bead, fiber, or membrane, comprising a porous support and a crosslinked polymer coating, wherein the polymer of the crosslinked polymer coating comprises at least one of polymerized monomer (A), at least one of polymerized monomer (B), at least one of polymerized monomer (C), wherein monomers (A)-(C) are as defined herein. Also disclosed are methods of preparing the porous medium and of treating a fluid containing a desired protein and one or more negatively charged species or of removing metals from organic solvents used in the microelectronics industry.

20 Claims, 6 Drawing Sheets

(56) References Cited

U.S. PATENT DOCUMENTS

| | | | |
|---|---|---|---|
| 9,022,227 B2 | 5/2015 | Na et al. | |
| 9,028,683 B2 | 5/2015 | Komiya et al. | |
| 9,272,246 B2 * | 3/2016 | Rasmussen | B01D 67/0093 |
| 9,433,904 B2 | 9/2016 | Demmer et al. | |
| 9,433,922 B2 | 9/2016 | Kozlov et al. | |
| 9,441,011 B2 | 9/2016 | Shinohara et al. | |
| 9,725,545 B2 * | 8/2017 | Wickert | B01D 15/00 |
| 9,758,547 B2 | 9/2017 | Rasmussen et al. | |
| 2004/0203149 A1 * | 10/2004 | Childs | B01D 69/10 |
| | | | 435/404 |
| 2010/0323430 A1 | 12/2010 | Kozlov | |
| 2011/0065900 A1 | 3/2011 | Johansson et al. | |
| 2012/0039920 A1 * | 2/2012 | Rasmussen | B01D 67/0006 |
| | | | 424/184.1 |
| 2012/0121819 A1 | 5/2012 | Kozlov et al. | |
| 2012/0168381 A1 | 7/2012 | Ramaswamy et al. | |
| 2012/0252091 A1 * | 10/2012 | Rasmussen | B01D 67/0093 |
| | | | 435/183 |
| 2012/0292244 A1 | 11/2012 | Harrold et al. | |
| 2013/0245139 A1 | 9/2013 | Kozlov et al. | |
| 2014/0238935 A1 | 8/2014 | Komkova et al. | |
| 2015/0136698 A1 * | 5/2015 | Bothof | B01J 20/321 |
| | | | 210/651 |
| 2015/0344520 A1 | 12/2015 | Matsumoto et al. | |
| 2016/0243503 A1 * | 8/2016 | Okabe | B01D 69/02 |
| 2016/0272676 A1 * | 9/2016 | Kozlov | C07K 1/34 |
| 2016/0367979 A1 | 12/2016 | Ashizawa et al. | |
| 2018/0311623 A1 * | 11/2018 | Okabe | B01D 69/02 |
| 2019/0329185 A1 * | 10/2019 | Jaber | B01D 67/0006 |

FOREIGN PATENT DOCUMENTS

| | | |
|---|---|---|
| CN | 107001410 A | 8/2017 |
| CN | 108136338 A | 6/2018 |
| EP | 0337144 A1 | 10/1989 |
| EP | 0347755 A2 | 12/1989 |
| EP | 1235748 | 5/2001 |
| EP | 1827691 | 4/2006 |
| EP | 2060316 A1 | 5/2009 |
| EP | 2143482 A1 | 1/2010 |
| EP | 2386628 A1 | 11/2011 |
| EP | 2691772 | 10/2012 |
| EP | 2961762 | 9/2014 |
| EP | 3116645 | 9/2015 |
| JP | H01-310744 A | 12/1989 |
| JP | 2006-519273 A | 8/2006 |
| JP | 2013-189427 A | 9/2013 |
| JP | 2016-510005 A | 4/2016 |
| JP | 2020-037100 A | 3/2020 |
| KR | 10-2005-0107440 A | 11/2005 |
| KR | 10-2011-0044882 A | 5/2011 |
| KR | 20140031231 A | 3/2014 |
| KR | 20150043271 A | 4/2015 |
| WO | 2004/073843 A1 | 9/2004 |
| WO | 2013/138098 A1 | 9/2013 |
| WO | WO 2014/134147 A1 | 9/2014 |
| WO | 2016/093926 A1 | 6/2016 |
| WO | WO 2017/029601 A1 | 2/2017 |
| WO | 2017/069965 A1 | 4/2017 |
| WO | WO 2017/205722 A1 | 11/2017 |

OTHER PUBLICATIONS

Intellectual Property Office of Singapore, Search Report in Application No. 10201907371Y (dated Jun. 22, 2020).
Korean Intellectual Property Office, Notice of Non-Final Rejection in Application No. 10-2019-0105044 (dated Sep. 1, 2020)
Japanese Patent Office, Notice of Reasons for Rejection in Japanese Patent Application No. 2019-143896 (dated Oct. 6, 2020).
Korean Intellectual Property Office, Notice of Allowance of Patent in Application No. 10-2019-105044 (dated Feb. 22, 2021).
Taiwan Intellectual Property Office, Examination Report including Search Report in TW Application No. 108130814 (dated Feb. 5, 2021).

* cited by examiner

SALT TOLERANT POROUS MEDIUM

BACKGROUND OF THE INVENTION

Production of monoclonal antibody (mAb) and purification thereof continue to pose a problem due to the high cost of the process. Contributing to the high cost are the several purification steps the biomolecules need to go through during isolation. For example, one of the purification steps is protein A affinity chromatography, wherein Staphylococcal protein A binds IgG molecules of subclasses 1, 2, and 4 with high selectivity and minimal interaction with the Fab region, the active region of the drug molecule. With the biotechnology market rapidly growing, improvements in these purification steps are becoming more desirable and more valuable in bringing biologics to the market in a timely space and at reduced cost.

During protein purification, polishing steps using ion exchanger media require that the media are not only selective to impurities but also tolerate feedstocks with high salt conductivities, for example, up to 15 mS/cm or more.

The foregoing shows that there exists an unmet need for ion exchanger media that are not only selective to impurities but also tolerate feedstocks with high salt conductivities.

In addition, there exists an unmet need for an ion exchanger medium for use in the microelectronic industry that can effectively remove trace metal ions from microelectronic wet etching chemicals (WEC) and in lithography processes.

BRIEF SUMMARY OF THE INVENTION

The present invention provides a porous media, e.g., beads, fibers, and membranes, comprising crosslinked polymers having negative charges. The media have salt tolerant properties and high dynamic binding capacities (DBC) for biologics, antibodies, and/or proteins, e.g., IgG, of up to 170 mg/mL at 10 CV/min flow rate. The porous media also have high capacity for removing metals present in organic solvents, e.g., organic solvents used in the microelectronics industry.

DETAILED DESCRIPTION OF THE INVENTION

Figure 1:
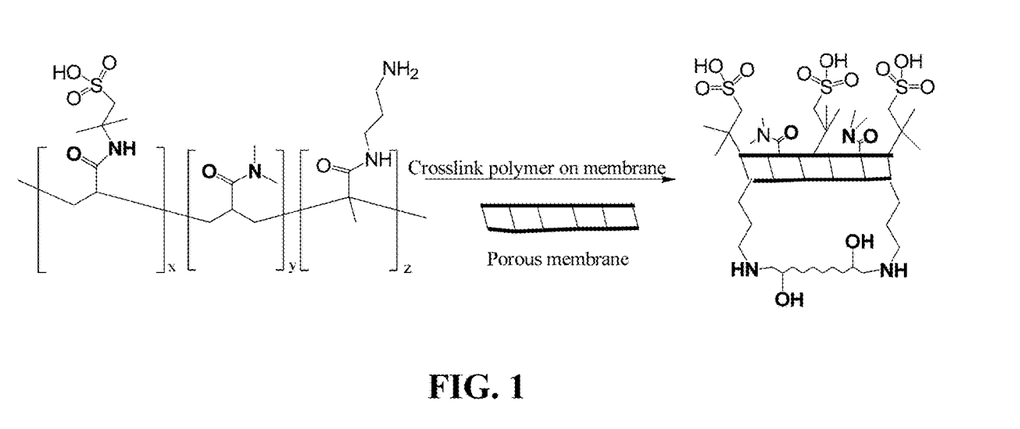
FIG. 1 schematically depicts the preparation of a porous medium, e.g., membrane, according to an embodiment of the invention.
Figure 2:
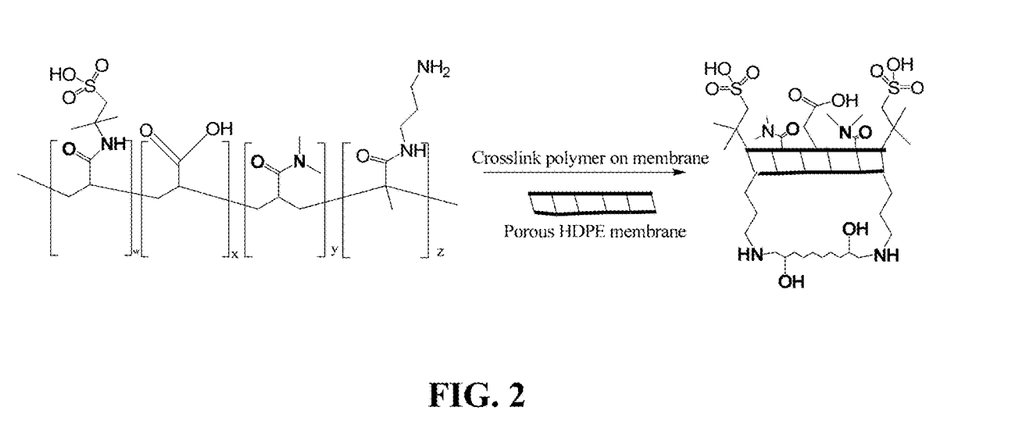
FIG. 2 depicts schematically depicts the preparation of a porous medium, e.g., membrane according to another embodiment of the invention.
Figure 3:
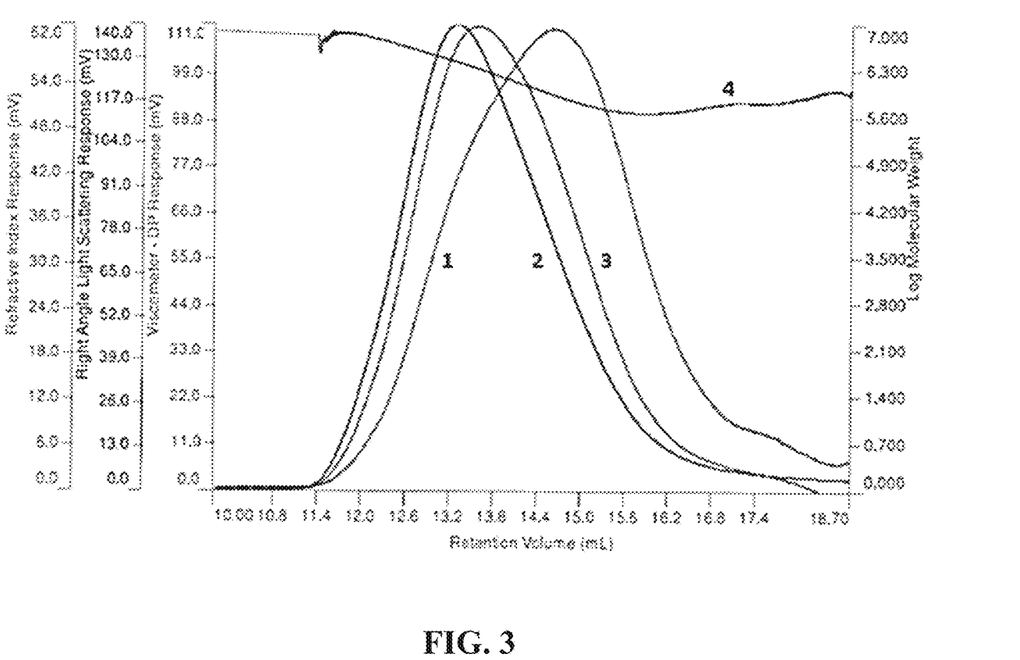
FIG. 3 depicts the triple detection elution profile for injection of poly(acrylamido-2-methylpropane sulfonate-co-(aminopropyl)methacrylamide-co-N,N-dimethylacrylamide) sample, wherein 1 represents the refractive index (RI), 3 represents the viscosity, 2 represents the relative angle laser light scattering (RALS) data, and 4 represents log MW.
Figure 4:
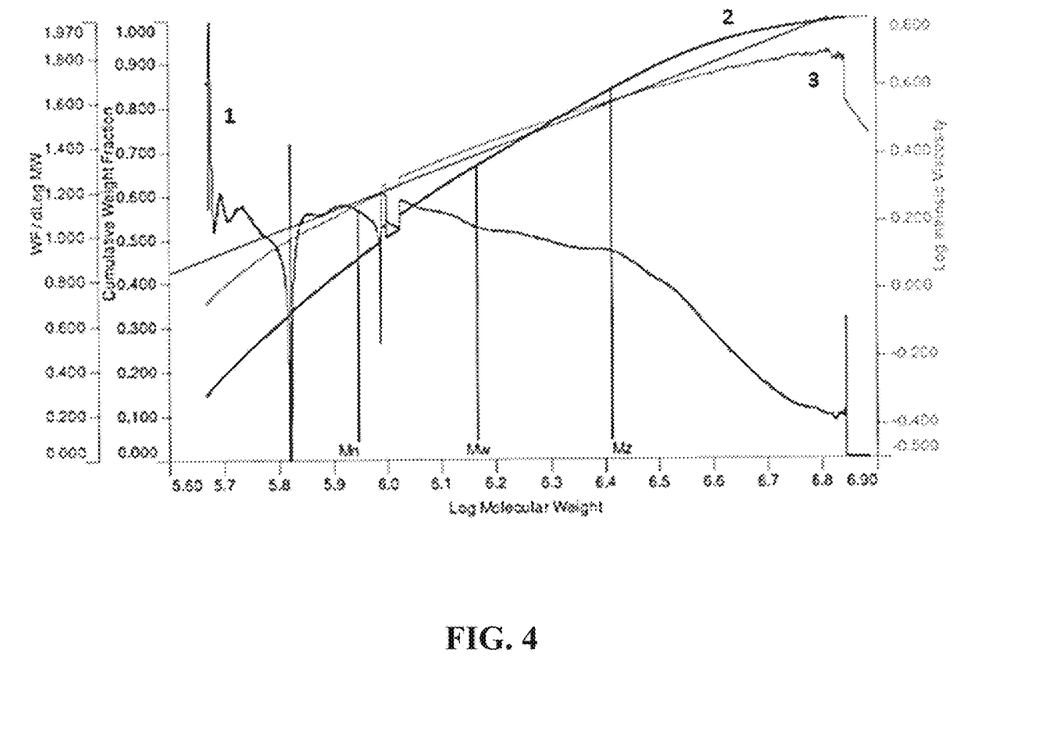
FIG. 4 depicts an overlay of the MW distribution plots obtained from the injection of a poly(acrylamido-2-methylpropane sulfonate-co-(aminopropyl)methacrylamide-co-N,N-dimethylacrylamide) sample, in accordance with an embodiment of the invention, wherein 1 represents the Normalized Weight Fraction (WF/d log MW), 2 represents Cumulative Weight Fraction, and 3 represents the Mark-Houwink-Sakurada plot ($\log([\eta])$ vs $\log(M)$).
Figure 5:
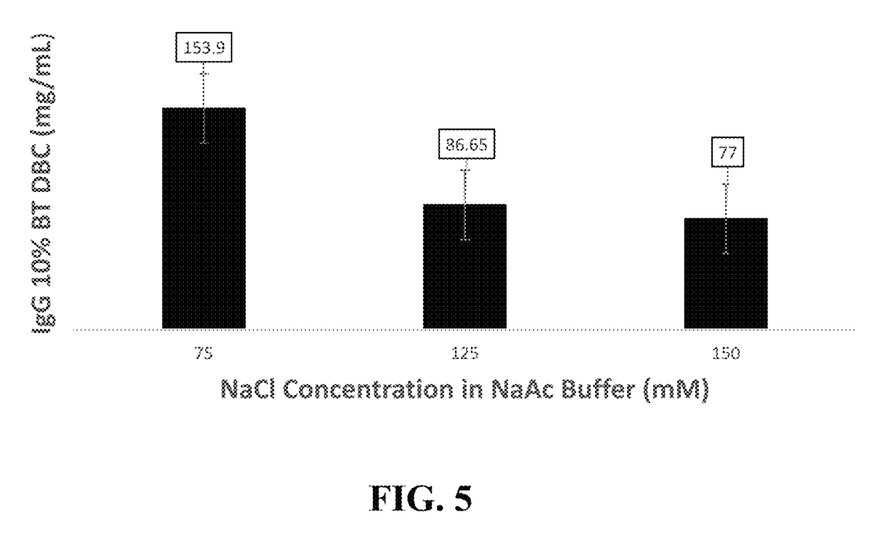
FIG. 5 depicts the IgG 10% breakthrough DBC of the porous membrane according to Example 8 at different salt concentrations.
Figure 6:
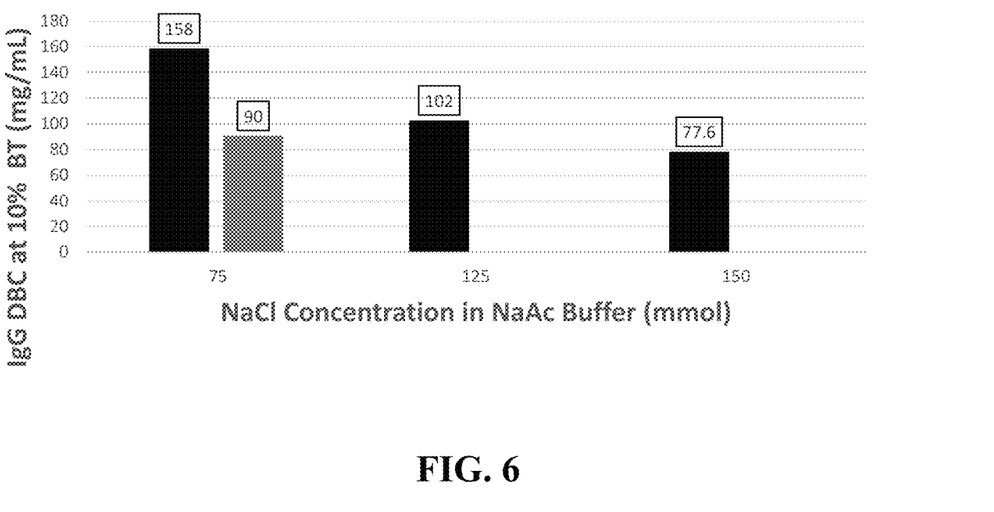
FIG. 6 depicts the IgG 10% breakthrough DBC of the porous membrane illustrated in FIG. 5 (solid black bar) vs. the breakthrough performance of a commercially available membrane (grey bar) Natrix Sb-HD.
Figure 7:
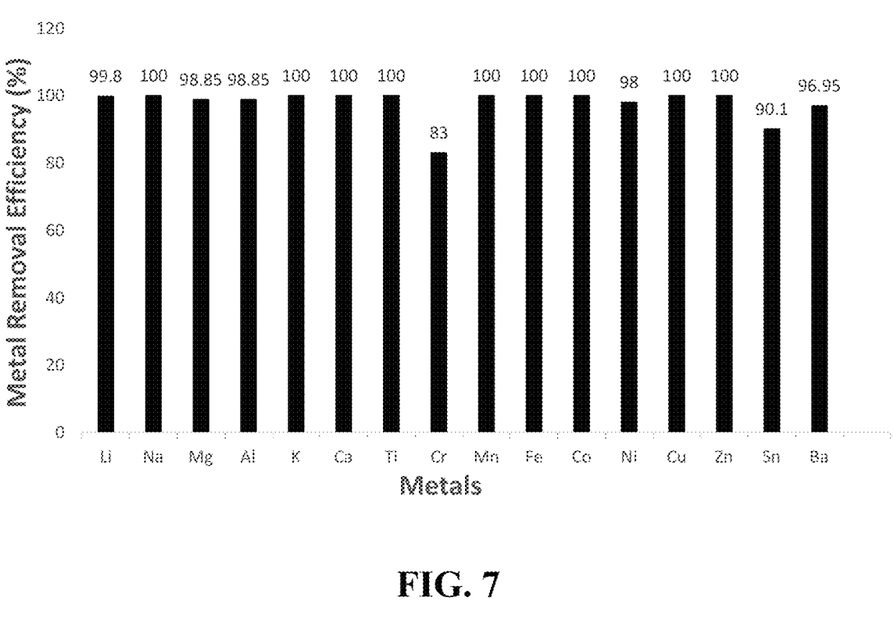
FIG. 7 depicts the trace metal removal efficiency of the porous membrane of Example 8.

The present invention provides a salt tolerant porous medium comprising a porous support and a crosslinked polymer coating, wherein the crosslinked polymer coating comprises at least one of polymerized monomer (A), at least one of polymerized monomer (B), and at least one of polymerized monomer (C), wherein monomer (A) has the formula:

wherein n is 1-6,
monomer (B) has the formula:

and
monomer (C) has the formula:

wherein m is 1-3 and X is $SO_3H$ or COOH;
wherein
$R^1$, $R^4$, and $R^8$ are independently H or $C_1$-$C_6$ alkyl, and $R^2$, $R^3$, $R^5$, $R^6$, and $R^7$ are independently H, $C_1$-$C_6$ alkyl, $C_6$-$C_{10}$ aryl, $C_1$-C alkoxy $C_1$-C alkyl, or triphenylmethyl.

In an embodiment, $R^1$ is $C_1$-$C_6$ alkyl and $R^4$ is H. In another embodiment, $R^1$ is $C_1$-$C_6$ alkyl, $R^4$ is H, and $R^8$ is H.

The $C_1$-$C_6$ alkyl group throughout this application can have 1, 2, 3, 4, 5, or 6 carbon atoms; the alkyl group can be linear or branched. Examples of alkyl groups include methyl, ethyl, n-propyl, i-propyl, n-butyl, i-butyl, t-butyl, n-pentyl, 2-methylbutyl, n-hexyl, 2-methylpentyl, and 3-methylpentyl.

In an embodiment of the invention, $R^1$ is methyl.

In any of the embodiments above, $R^2$ and $R^3$ are H, and $R^5$ and $R^6$ are independently $C_1$-$C_6$ alkyl, In any of the embodiments above, $R^2$ and $R^3$ are H, and $R^5$ and $R^6$ are methyl.

In any of the embodiments above, $R^2$, $R^3$, $R^5$, and $R^6$ are independently H, methyl, phenyl, methoxy methyl, or triphenylmethyl.

In certain embodiments, $R^2$ and $R^3$ are H, and $R^5$ and $R^6$ are independently methyl, phenyl, methoxy methyl, or triphenylmethyl.

In any of the embodiments above, $R^7$ is alkyl, preferably methyl.

In any of the embodiments above, the copolymer comprises one polymerized monomer (A), one polymerized monomer (B), and one polymerized monomer (C).

In any of the embodiments above, the copolymer comprises one polymerized monomer (A), one polymerized monomer (B), and two different polymerized monomers (C).

In any of the embodiments above, X in one of the polymerized monomers (C) is $SO_3H$ and X in the other polymerized monomer (C) is COOH.

In an embodiment, the medium is a porous membrane.

In another embodiment, the medium is a bead or fiber.

The ion exchange polymers for use in the porous medium can be prepared from any suitable combination of monomers, e.g., N,N-dimethylacrylamide, N-(3-aminopropyl)methacrylamide and 2-acrylamido-2-methylpropane sulfonate, 2-acrylamido-2-methylpropane sulfonate, N-(3-aminopropyl)methacrylamide and N-isopropylacrylamide, 2-acrylamido-2-methylpropane sulfonate, N-(3-aminopropyl)methacrylamide and tert-butylacrylamide, 2-acrylamido-2-methylpropane sulfonate, N-(3-aminopropyl)methacrylamide and ethylacrylamide, 2-acrylamido-2-methylpropane sulfonate, N-(3-aminopropyl)methacrylamide and phenylacrylamide, 2-acrylamido-2-methylpropane sulfonate, N-(3-aminopropyl)methacrylamide and diethyl acrylamide, 2-acrylamido-2-methylpropane sulfonate, N-(3-aminopropyl)methacrylamide and N-(isobutoxy methyl)acrylamide, 2-acrylamido-2-methylpropane sulfonate, N-(3-aminopropyl)methacrylamide and N-(triphenylmethyl)acrylamide, 2-acrylamido-2-methylpropane sulfonate, N-(3-aminopropyl)methacrylamide and N,N-dimethylacrylamide, 2-acrylamido-2-methylpropane sulfonate, N-(2-aminoethyl)methacrylamide and N-isopropylacrylamide, 2-acrylamido-2-methylpropane sulfonate, N-(2-aminoethyl)methacrylamide and tertbutyl acrylamide, 2-acrylamido-2-methylpropane sulfonate, N-(2-aminoethyl)methacrylamide and phenylacrylamide, 2-acrylamido-2-methylpropane sulfonate, N-(2-aminoethyl)methacrylamide and diethyl acrylamide, 2-acrylamido-2-methylpropane sulfonate, N-(2-aminoethyl)methacrylamide and ethyl acrylamide, 2-acrylamido-2-methylpropane sulfonate, N-(2-aminoethyl)methacrylamide and N-(isobutoxymethyl)methacrylamide, 2-acrylamido-2-methylpropane sulfonate, N-(2-aminoethyl)methacrylamide and N-(triphenylmethyl)acrylamide, and 2-acrylamido-2-methylpropane sulfonate, N-(2-aminoethyl)methacrylamide and N,N-dimethylacrylamide.

The invention provides, in embodiments, one or more of the following:

A terpolymer comprising 2-acrylamido-2-methylpropane sulfonate, N-(3-aminopropyl)methacrylamide and N-dimethylacrylamide, A terpolymer comprising acrylic acid, N-(3-aminopropyl) methacrylamide and N-dimethylacrylamide, A terpolymer comprising 2-acrylamido-2-methylpropane sulfonate, N-(3-aminopropyl)methacrylamide and N-dimethylacrylamide and crosslinked on a medium using the terpolymer's primary amine moiety, A terpolymer comprising 2-acrylamido-2-methylpropane sulfonate, an amino alkyl methacrylamide and N-dimethylacrylamide, and crosslinked on a medium using the terpolymer's primary amine moiety, A terpolymer comprising acrylic acid, N-(3-aminopropyl) methacrylamide and N-dimethylacrylamide, and crosslinked on a medium using the primary terpolymer's amine moiety, A terpolymer comprising 2-acrylamido-2-methylpropane sulfonate, N-(3-aminopropyl)methacrylamide, N-dimethyl acrylamide or any alkylacrylamide e.g., N-tert-butyl acrylamide, N-phenylacrylamide, N-diethylacrylamide, N-isopropylacrylamide, N-ethylacrylamide, N-diethylmethacrylamide, N-(isobutoxymethyl) methacrylamide, and N-(triphenylmethyl)methacrylamide, and crosslinked on a medium using the terpolymer's primary amine moiety, A salt-tolerant, ion-exchange porous membrane derived from a terpolymer comprising 2-acrylamido-2-methylpropane sulfonate, N-(3-aminopropyl)methacrylamide, N,N-dimethyl acrylamide or any alkylacrylamide e.g., N-tert-butyl acrylamide, N-phenylacrylamide, N,N-diethylacrylamide, N-isopropylacrylamide, N-ethylacrylamide, N,N-diethylmethacrylamide, N-(isobutoxymethyl)methacrylamide, and N-(triphenylmethyl) methacrylamide, and crosslinked on a medium using the terpolymer's primary amine moiety that advantageously can be used for, e.g., capture of monoclonal antibody, polishing of monoclonal antibodies, or viral vector purification, A salt-tolerant, ion-exchange porous membrane, where the salt tolerant properties of the terpolymer coated on the porous membrane are advantageously imparted by alkyl acrylamide portion of the polymer, A terpolymer comprising 2-acrylamido-2-methylpropane sulfonate, N-(3-aminopropyl)methacrylamide, N-dimethyl acrylamide or any alkylalcrylamide e.g., N-tert-butyl acrylamide, N-phenylacrylamide, N,N-diethylacrylamide, N-isopropylacrylamide, N-ethylacrylamide, N,N-diethylmethacrylamide, N-(isobutoxymtheyl)methacrylamide, and N-(triphenylmethyl) methacrylamide, and crosslinked on a medium using the primary amine moiety to form cation-exchange porous membrane, that advantageously can be used for, e.g., capturing of trace metal contaminants in Micro E solvents, A terpolymer comprising acrylic acid, N-(3-aminopropyl) methacrylamide, and N-dimethyl acrylamide, A terpolymer comprising acrylic acid, N-(3-aminopropyl) methacrylamide and N,N-dimethyl acrylamide, and crosslinked on a medium using the terpolymer's primary amine moiety, A tetrapolymer comprising 2-acrylamido-2-methylpropane sulfonate, N-(3-aminopropyl)methacrylamide, N,N-dimethylacrylamide and N-tert-butyl acrylamide, A tetrapolymer comprising 2-acrylamido-2-methylpropane sulfonate, N-(3-aminopropyl)methacrylamide, N,N-dimethylacrylamide, and styrene sulfonic acid, A tetrapolymer comprising 2-acrylamido-2-methylpropane sulfonate, N-(3-aminopropyl)methacrylamide, N,N-dimethylacrylamide, and N-tert-Butyl acrylamide and crosslinked on a medium using the tetrapolymer's primary amine moiety, A tetrapolymer comprising 2-acrylamido-2-methylpropane sulfonate, N-(3-aminopropyl)methacrylamide, N,N-dimethylacrylamide and styrene sulfonic acid and crosslinked on a medium using the tetrapolymer's primary amine moiety, A tetrapolymer comprising 2-acrylamido-2-methylpropane sulfonate, N-(3-aminopropyl)methacrylamide, N,N-dimethylacrylamide and acrylic acid; and A tetrapolymer comprising 2-acrylamido-2-methylpropane sulfonate, N-(3-aminopropyl)methacrylamide, N,N-dimethylacrylamide and acrylic acid, and crosslinked on a medium using the tetrapolymer's primary amine moiety.

The molecular weight ranges of the copolymers can be of any suitable range, for example, from 50 to 4000 kD, 100 to 3500 kD, or 200 to 1500 kD, 50 to 3126 kD. Most preferred molecular weight range is from 207 kD to 1270 kD, and in embodiments, from 50 to 3126 kD, and preferably from 207 kD to 1270 kD, wherein the molecular weight is as determined by triple detection GPC analysis.

The co-monomers can be present in the copolymer in any suitable molar ratios, e.g., ranges of monomer combination that provide high salt tolerance in chromatographic applications, in particular terpolymers comprising 2-acrylamido-2-methylpropane sulfonate, N-(3-aminopropyl)methacrylamide, and dimethylacrylamide are from molar ratios of 1:0.1:1 to molar ratios of 5:0.5:2.

In embodiments, the ranges of monomer combinations that provide high ion exchange capacities for metal ion removal in microelectronics solvent application, in particular for the combination of monomers comprising 2-acrylamido-2-methylpropane sulfonate, N-(3-aminopropyl) methacrylamide and any alkylacrylamide (such as N-tert-butyl acrylamide, N-phenylacrylamide, N,N-diethylacrylamide, N-isopropylacrylamide, N-ethylacrylamide, N,N-diethylmethacrylamide, N-(isobutoxymethyl)methacrylamide, acrylamide, and N-(triphenylmethyl)methacrylamide) are from molar ratios of 1:0.1:1 to molar ratios of 5:0.5:2.

In embodiments, for membrane applications, the ranges of monomer combination that impact salt tolerance in chromatographic application while still permitting efficient recovery of the protein are from mol ratios of 1:0.25:2 to mol ratios of 2:0.5:1. This range is applicable in particular when ter-monomers comprising 2-acrylamido-2-methylpropane sulfonate, N-(3-aminopropyl)methacrylamide and any alkylacrylamide (such as N,N-dimethylacrylamide, N-tert-butyl acrylamide, N-phenylacrylamide, N,N-diethylacrylamide, N-isopropylacrylamide, N-ethylacrylamide, N,N-diethylmethacrylamide, N-(isobutoxymethyl)methacrylamide, acrylamide, and N-(triphenylmethyl)methacrylamide) are used to form a polymer crosslinked on a membrane.

In embodiments, where ter-monomers of 2-acrylamido-2-methylpropane sulfonate, N-(3-aminopropyl)methacrylamide, and N,N-dimethylacrylamide are used to form a polymer crosslinked on a membrane for protein purification, the ranges of polymer concentrations that impart high salt tolerance, while simultaneously providing high dynamic binding capacities up to 200 mg/ml IgG, are from 1%-10% by weight.

The present invention further provides a method for producing a porous medium, comprising:
(i) polymerizing a mixture of monomers (A), (B), and (C) to obtain a terpolymer, and
(ii) coating the terpolymer obtained in (i) on a porous support with in situ crosslinking to obtain a copolymer coating disposed on the porous support.

Polymerization of the monomers can be carried out by using suitable initiators—free radical, cationic, or anionic initiators, and in particular, free radical initiators, for example, thermally activated free radical initiators such as azo compounds, persulfates, peroxides, peracids, peracetates, and organometallics. Examples of free radical initiators include AIBN, 4,4-azobis(4-cyanovaleric acid), 1,1'-azobis(cyclohexanecarbonitrile), benzoyl peroxide, 2,2-bis(tert-butylperoxy)butane, 1,1-bis(tert-butylperoxy)cyclohexane, dicumylperoxie, tert-butyl peroxybenzoate, tert-amyl peroxybenzoate, and potassium persulfate.

In accordance with the method, the crosslinking agent comprises two or more groups, for example, 2, 3, 4, or more crosslinking functional groups, e.g., a crosslinking agent selected from diepoxides, dialdehydes, dihalides, and diesters. For example, the crosslinking agent is selected from ethylene glycol diglycidyl ether, propylene glycol diglycidyl ether, glyceryl triglycidyl ether, polyethylene glycol diglycidyl ether, glycol dimesylate ester, and ditosylate ester, and any combination thereof.

The present invention further provides a method of treating a fluid containing trace metals, the method comprising contacting the fluid with the medium or with the porous membrane, as described above, and recovering a fluid containing a reduced concentration of trace metals.

In accordance with an embodiment of the invention, the porous membrane can be a nanoporous membrane, for example, a membrane having pores of diameter between 1 nm and 100 nm, or a microporous membrane, for example, a membrane having pores of diameter between 0.005 μm and 10 μm.

The porous support on which the coating is provided can be of any suitable material, e.g., a polymer, metallic, or ceramic, and in particular a polymer, for example, polysulfone (PSU), polyethersulfone (PES), polyphenyl ether (PPE), polyphenylene ether sulfone (PPES), polyphenylene oxide (PPO), polycarbonate (PC), poly(phthalazinone ether sulfone ketone) (PPESK), polyether ether ketone (PEEK), polyether ketone ketone (PEKK), polyetherimide (PEI) and blends thereof.

In an embodiment, the copolymer is coated and crosslinked on porous high density polyethylene membranes, polyether sulfone membranes, polyvinylidene fluoride membrane, polytetrafluoroethylene membrane, polyphenylsulfone membrane, polyphenylene sulfide membrane, polyethylene and polypropylene membranes, polyester membranes, melt blown polyester membranes, melt blown polypropylene membranes, cellulose membranes, nylon membranes, and polyvinylchloride/acrylonitrile, to produce porous media or membranes.

The porous media according to embodiments of the invention can be disposed in a housing comprising at least one inlet and at least one outlet and defining at least one fluid flow path between the inlet and the outlet, wherein at least one inventive membrane or a filter including at least one inventive membrane is across the fluid flow path, to provide a filter device or filter module. In an embodiment, a filter device is provided comprising a housing comprising an inlet and a first outlet, and defining a first fluid flow path between the inlet and the first outlet; and at least one inventive membrane or a filter comprising at least one inventive membrane, the inventive membrane or filter comprising at least one inventive membrane being disposed in the housing across the first fluid flow path.

For crossflow applications, in an embodiment, at least one inventive porous membrane or filter comprising at least one inventive membrane is disposed in a housing comprising at least one inlet and at least two outlets and defining at least a first fluid flow path between the inlet and the first outlet, and a second fluid flow path between the inlet and the second outlet, wherein the inventive membrane or filter comprising at least one inventive membrane is across the first fluid flow path, to provide a filter device or filter module. In an illustrative embodiment, the filter device comprises a crossflow filter module, the housing comprising an inlet, a first outlet comprising a concentrate outlet, and a second outlet comprising a permeate outlet, and defining a first fluid flow path between the inlet and the first outlet, and a second fluid flow path between the inlet and the second outlet, wherein at least one inventive membrane or filter comprising at least one inventive membrane is disposed across the first fluid flow path.

The filter device or module may be sterilizable. Any housing of suitable shape and providing an inlet and one or more outlets may be employed.

The housing can be fabricated from any suitable rigid impervious material, including any impervious thermoplastic material, which is compatible with the fluid being processed. For example, the housing can be fabricated from a metal, such as stainless steel, or from a polymer, e.g., transparent or translucent polymer, such as an acrylic, polypropylene, polystyrene, or a polycarbonate resin.

The following examples further illustrate the invention but, of course, should not be construed as in any way limiting its scope.

Example 1

This example illustrates a method of preparation of a terpolymer solution in accordance with an embodiment of the invention.

Preparation of a 10% solution of the terpolymer, poly(acrylamido-2-methylpropane sulfonate-co-(aminopropyl)methacrylamide-co-N,N-dimethylacrylamide): 2-acrylamido-2-methylpropane sulfonate (15.6 g, 75 mM), N-(3-aminopropyl)methacrylamide hydrochloride (4.5 g, 25 mM) and N,N-dimethylacrylamide (10 g, 100 mM) were mixed with DI water (260 g) and 8 M NaOH (17.1 g), the mixture was degassed for 5 minutes, and ammonium persulfate (0.690 g, 3 mM) was added and mixed. The reaction mixture was stirred at 60° C. for 2 hours under nitrogen gas and allowed to cool to room temperature to obtain the terpolymer solution.

Example 2

This example illustrates a method of preparation of a terpolymer solution in accordance with another embodiment of the invention.

Preparation of a 10% solution of poly(styrene sulfonic acid-co-(aminopropyl)methacrylamide-co-N,N-dimethylacrylamide): Sodium 4-vinylbenzenesulfonic acid (15.46 g, 75 mM), N-(3-aminopropyl)methacrylamide hydrochloride (4.5 g, 25 mM) and N,N-dimethylacrylamide (10 g, 100 mM) were mixed with DI water (260 g) and 8 M NaOH (17.1 g), the mixture was degassed for 5 minutes, and ammonium persulfate (0.690 g, 3 mM) was added. The reaction mixture was stirred at 60° C. for 2 hours under nitrogen gas and allowed to cool to room temperature, to obtain the terpolymer solution.

Example 3

This example illustrates a method of preparation of a tetrapolymer solution in accordance with another embodiment of the invention.

Preparation of poly(acrylamido-2-methylpropane sulfonate-co-(aminopropyl)methacrylamide-co-N,N-dimethylacrylamide-co-tert-butylacrylamide), 9.5% solution: 2-acrylamido-2-methylpropane sulfonate (10.45 g, 50 mM), N-(3-aminopropyl)methacrylamide hydrochloride (2.24 g, 12.5 mM), N,N-dimethylacrylamide (5 g, 50 mM), and tert-butylacrylamide [1.6 g, 12.6 mM in IPA (9 g)] were mixed with DI water (164.7 g) and 8 M NaOH (10 g), the mixture degassed for 5 minutes, and ammonium persulfate (0.431 g, 1.9 mM) was added. The reaction mixture was stirred at 60° C. for 2 hours under nitrogen gas and allowed to cool to room temperature to obtain the above tetrapolymer solution.

Example 4

This example illustrates a method of preparation of a tetrapolymer solution in accordance with yet another embodiment of the invention.

Preparation of poly(acrylamido-2-methylpropane sulfonate-co-(aminopropyl)methacrylamide-co-N,N-dimethylacrylamide-co-acrylic acid), 10% solution: 2-acrylamido-2-methylpropane sulfonate (7.3 g, 35.3 mM), N-(3-aminopropyl)methacrylamide hydrochloride (2.52 g, 14.1 mM), N,N-dimethylacrylamide (7 g, 70.6 mM), and acrylic acid [2.54 g, 35.3 mM and IPA (9 g)] were mixed in DI water (155 g) and 8 M NaOH (10 g), the mixture was degassed for 5 minutes, and ammonium persulfate (0.532 g, 2.3 mM) was added. The reaction mixture was stirred at 60° C. for 2 hours under nitrogen gas and allowed to cool to room temperature to obtain the above tetrapolymer solution.

Example 5

This example illustrates a method of preparation of a tetrapolymer solution in accordance with a further embodiment of the invention.

Preparation of poly(acrylamido-2-methylpropane sulfonate-co-(aminopropyl)methacrylamide-co-N,N-dimethylacrylamide-co-styrene sulfonic acid), 8% solution: Sodium 4-vinylbenzenesulfonic acid (4.16 g, 20 mM), N-(3-aminopropyl)methacrylamide hydrochloride (1.8 g, 10 mM), 2-acrylamido-2-methylpropane sulfonate (4.18 g, 20 mM), and N,N-dimethylacrylamide (4 g, 40 mM) were mixed in DI-water (156.34 g) with 8 M NaOH (17.1 g), degassed for 5 minutes, followed by the addition of ammonium persulfate (0.690 g, 3 mM). The reaction mixture was stirred at 60° C. for 2 hours under nitrogen gas and allowed to cool to room temperature to obtain the above polymer solution.

Example 6

This example illustrates a method of preparation of a porous membrane in accordance with an embodiment of the invention.

5% Sulfonated Polymer Coating (100 g mix): The 10% sulfonated polymer (50 g) from Example 1 was mixed with water (49 g), polyethylene glycol diglycidyl ether (150 mg), and Triton X-100 (850 mg), and stirred until dissolved. The pH of the solution was adjusted to 10 with aqueous NaOH to obtain a coating solution. A HDPE membrane of 3 μm pore diameter was coated with the coating solution by dip coating. The coated membrane was sandwiched between two pipettes and scraped from top to bottom to provide a thin coating on the HDPE membrane. The coating on the membrane was allowed to crosslink at 65° C. for one hour or at room temperature overnight. The resulting membrane was leached in cold water for 24 hours and allowed to dry.

Example 7

This example illustrates a method of preparation of a porous membrane in accordance with another embodiment of the invention.

2-Acrylamido-2-methylpropane sulfonate (104.5 g, 504 mmol) was mixed with N,N-dimethylacrylamide (50 g, 504 mmol), N-(3-aminopropyl)methacrylamide HCl (22.4 g, 126 mmol), and DI water (1.524 kg) with 170 g of isopropanol. The pH of the mixture was adjusted to 9.6 with 8 M NaOH (100 g). The reaction mixture was degassed with nitrogen gas for 15 minutes, and ammonium persulfate (3.88 g 1.5 mol %) was added. The mixture was stirred at 60° C. for 2 hours, and cooled to room temperature to obtain a 10% polymer solution.

A 4% polymer coating solution was prepared from the above 10% polymer solution with 0.85% Triton X100 surfactant and 0.45% diepoxide crosslinker, polyethylene glycol diglycidyl ether. The pH of the solution was adjusted to 10 and a HDPE membrane of 3 μm pore diameter was dip-coated in the above solution. The coated membrane was thermally crosslinked at 65° C. for one hour, leached in DI water overnight, and dried at 65° C. overnight.

Example 8

This example illustrates the ability of membranes in accordance with an embodiment to remove trace metals.

Baseline: 0.2 μm Membrane samples were flushed with 100 mL of IPA (10 mL/min), 200 mL of DIW, 100 mL of 5% HCl, 200 mL DI Water, and 200 mL of IPA. A 100 mL sample was collected, and metal analysis was conducted with ICP-MS.

Metal challenge: 0.2 μm Membrane samples from Example 7 were challenged with spiked IPA (1 ppb of metals) at an effluent rate of 7 mL/min. The first 10 mL of effluent was discarded, and the next 10 mL effluent was collected into PFA bottles. Metal analysis was conducted with ICP-MS. This experiment was repeated for n=2.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A porous medium comprising a porous support and a crosslinked polymer coating,
wherein the crosslinked polymer coating is prepared by polymerizing a monomer mixture of at least one monomer (A), at least one monomer (B), and at least one monomer (C), and a crosslinking agent selected from proplene glycol diglycidyl ether, glyceryl triglycidyl ether, polyethylene glycol diglycidyl ether, dialdehyde, dihalide, diester, disulfonyl chloride, and diacyl halide,
wherein
monomer (A) has the formula:

$$CH_2=C(R^1)-C(=O)-NH-(CH_2)_n-N'R^2R^3,$$

wherein n is 1-6,
monomer (B) has the formula:

$$CH_2=C(R^4)-C(=O)-NR^5R^6,$$

and
monomer (C) has the formula:

$$CH_2=C(R^8)-C(=O)-NH-C(R^7)_2-(CH_2)_m-X,$$

wherein m is 1-3 and X is $SO_3H$ or COOH;
wherein
$R^1$, $R^4$, and $R^8$ are independently H or $C_1$-$C_6$ alkyl, and $R^2$, $R^3$, $R^5$, $R^6$, and $R^7$ are independently H, $C_1$-$C_6$ alkyl, $C_6$-$C_{10}$ aryl, ($C_1$ or $C_2$) alkoxy ($C_1$ or $C_2$) alkyl, or triphenylmethyl.

2. The porous medium of claim 1, wherein $R^1$ is $C_1$-$C_6$ alkyl and $R^4$ is H.

3. The porous medium of claim 1, wherein $R^1$ is methyl.

4. The porous medium of claim 1, wherein $R^2$ and $R^3$ are H, and $R^5$ and $R^6$ are independently $C_1$-$C_6$ alkyl.

5. The porous medium of claim 1, wherein $R^2$ and $R^3$ are H, and $R^5$ and $R^6$ are methyl.

6. The porous medium of claim 1, wherein $R^2$, $R^3$, $R^5$, and $R^6$ are independently H, methyl, phenyl, methoxy methyl, or triphenylmethyl.

7. The porous medium of claim 1, wherein $R^2$ and $R^3$ are H, and $R^5$ and $R^6$ are independently methyl, phenyl, methoxy methyl, or triphenylmethyl.

8. The porous medium of claim 1, wherein $R^7$ is alkyl.

9. The porous medium of claim 8, wherein $R^7$ is methyl.

10. The porous medium of claim 1, wherein the monomer mixture is a mixture of one monomer (A), one monomer (B), and one monomer (C).

11. The porous medium of claim 1, wherein the monomer mixture is a mixture of one monomer (A), one monomer (B), and two different monomers (C).

12. The porous medium of claim 11, wherein X in one of the polymerized monomers (C) is $SO_3H$ and X in the other polymerized monomer (C) is COOH.

13. The porous medium of claim 1, which is a porous membrane.

14. The porous medium of claim 1, which is a bead or fiber.

15. A method for producing a porous medium according to claim 1, comprising:
(i) polymerizing a mixture of one or more of each of monomers (A), (B), and (C), to obtain a polymer and (ii) coating the polymer obtained in (i) on a porous support with the crosslinking agent and crosslinking in situ to obtain a crosslinked polymer coating disposed on the porous support.

16. The method of claim 15, wherein the crosslinking agent is selected from propylene glycol diglycidyl ether, glyceryl triglycidyl ether, polyethylene glycol diglycidyl ether, glycol dimesylate ester, and glycol dimesoyl chloride, ditosylate ester, and any combination thereof.

17. A method of treating a fluid containing a desired protein and one or more impurities, the method comprising contacting the fluid with the porous medium of claim 1 and recovering the desired protein with a reduced concentration of the impurities.

18. The method of claim 17, wherein the desired protein is an antibody or a biologic.

19. A method of treating a fluid containing trace metals, the method comprising contacting the fluid with the porous medium of claim 1 and recovering a fluid containing a reduced concentration of trace metals.

20. The porous medium of claim 1, wherein the crosslinking agent is selected from propylene glycol diglycidyl ether, glyceryl triglycidyl ether, polyethylene glycol diglycidyl ether, glycol dimesylate ester, and glycol dimesoyl chloride, ditosylate ester, and any combination thereof.

* * * * *